(12) United States Patent
Wang et al.

(10) Patent No.: US 12,260,578 B2
(45) Date of Patent: Mar. 25, 2025

(54) ULTRASOUND IMAGE ACQUISITION METHOD, SYSTEM AND COMPUTER STORAGE MEDIUM

(71) Applicant: SHENZHEN MINDRAY BIO-MEDICAL ELECTRONICS CO., LTD., Guangdong (CN)

(72) Inventors: Bo Wang, Shenzhen (CN); Longfei Cong, Shenzhen (CN); Lei Zhu, Shenzhen (CN); Weihua Song, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 780 days.

(21) Appl. No.: 17/350,272

(22) Filed: Jun. 17, 2021

(65) Prior Publication Data
US 2021/0383564 A1 Dec. 9, 2021

Related U.S. Application Data

(63) Continuation of application No. PCT/CN2018/114916, filed on Nov. 9, 2018.

(51) Int. Cl.
*A61B 8/08* (2006.01)
*A61B 8/00* (2006.01)
(Continued)

(52) U.S. Cl.
CPC .............. *G06T 7/70* (2017.01); *A61B 8/0833* (2013.01); *A61B 8/463* (2013.01); *A61B 8/466* (2013.01);
(Continued)

(58) Field of Classification Search
None
See application file for complete search history.

(56) References Cited

U.S. PATENT DOCUMENTS

| 7,346,381 B2 | 3/2008 | Okerlund et al. |
| 9,430,879 B2 | 8/2016 | Tian et al. |
| (Continued) | | |

FOREIGN PATENT DOCUMENTS

| CN | 1503184 A | 6/2004 |
| CN | 102081697 A | 6/2011 |
| (Continued) | | |

OTHER PUBLICATIONS

"EAE/ASE Recommendations for Image Acquisition and Display Using Three-Dimensional Echocardiography" (published in Jan. 2012) https://www.sciencedirect.com/science/article/pii/S089473171100842X?via%3Dihub.*

(Continued)

*Primary Examiner* — Rinna Yi
(74) *Attorney, Agent, or Firm* — Sheppard Mullin Richter & Hampton LLP

(57) ABSTRACT

An ultrasound image acquisition method, comprising: according to a first collection instruction, determining a working mode of an ultrasound image acquisition system to be a first mode; in the first mode, transmitting a first ultrasound wave to interior of a to-be-detected object; obtaining a first ultrasound echo signal based on the first ultrasound wave that is returned from the interior of the to-be-detected object, and combining beams thereof to obtain first basic ultrasound wave images; according to the first basic ultrasound images, acquiring a first reference direction and the contour of a reference to-be-detected sub-object; according to the first reference direction and the contour of the reference to-be-detected sub-object, acquiring first spatial position information of the interior of the to-be-detected object; according to the first spatial position information, generating and displaying a first stereoscopic ultra- (Continued)

sound image and/or a first planar ultrasound image based on the interior of the to-be-detected object.

15 Claims, 10 Drawing Sheets

(51) Int. Cl.
    *G06T 7/00*     (2017.01)
    *G06T 7/70*     (2017.01)
    *G06T 15/08*     (2011.01)

(52) U.S. Cl.
    CPC ............... *A61B 8/483* (2013.01); *A61B 8/54* (2013.01); *G06T 7/0012* (2013.01); *G06T 15/08* (2013.01); *G06T 2207/10136* (2013.01); *G06T 2207/30048* (2013.01)

(56) References Cited

U.S. PATENT DOCUMENTS

| | | | |
|---|---|---|---|
| 9,721,355 B2 | 8/2017 | Tian et al. | |
| 2008/0114244 A1 | 5/2008 | Murashita et al. | |
| 2008/0317316 A1* | 12/2008 | Ohuchi | A61B 8/08 382/131 |
| 2009/0203996 A1* | 8/2009 | Thiele | A61B 8/466 600/447 |
| 2009/0209859 A1* | 8/2009 | Tsujita | A61B 8/08 600/445 |
| 2014/0176561 A1 | 6/2014 | Nakamura | |
| 2015/0248750 A1* | 9/2015 | Tsujita | A61B 5/0059 382/131 |
| 2018/0042573 A1* | 2/2018 | Fukuda | A61B 8/5223 |

FOREIGN PATENT DOCUMENTS

| | | |
|---|---|---|
| CN | 102397082 A | 4/2012 |
| CN | 103747740 A | 4/2014 |

OTHER PUBLICATIONS

PCT International Search Report and the Written Opinion mailed Aug. 8, 2019, issued in related International Application No. PCT/CN2018/114916, with English translation (13 pages).

\* cited by examiner

```
based on a received first acquisition instruction used for collecting an object to be detected,    ╱─201
  setting the operating mode of the ultrasound image acquisition system as a first mode acquiring first spatial position information inside the object to be detected in the first mode   ╱─202
```

ULTRASOUND IMAGE ACQUISITION METHOD, SYSTEM AND COMPUTER STORAGE MEDIUM

CROSS-REFERENCE TO RELATED PATENT APPLICATION

This application is a continuation of International Patent Application No. PCT/CN2018/114916, filed with the China National Intellectual Property Administration (CNIPA) on Nov. 9, 2018. The content of the above application is incorporated herein by reference in its entirety.

TECHNICAL FIELD

The present disclosure relates to ultrasound imaging, in particular to an ultrasound image acquisition method, system, and computer storage medium.

BACKGROUND OF THE INVENTION

With medical technology developing and improving continuously, four dimensional (4D) ultrasound technology can display three-dimensional structures of organs like the heart in real time, showing the location, shape, size of a lesion and the special adjacency between the lesion and its surrounding from any cut and angle. Therefore, 4D ultrasound technology is increasingly used in diagnosis and guidance of designated surgical plans.

However, the use of 4D ultrasound technology may produce a large amount of data; it is because an operator generally analyzes generated image data manually to obtain the internal spatial position information of organs including the heart; this leading to a large workload for the operator, and inaccurate analysis of the image data may result in incorrect spatial location information.

SUMMARY OF THE INVENTION

In view of this, with ultrasound image acquisition methods, systems, and computer storage medium provided in the embodiments of the present disclosure, a problem that an operator needs to manually analyze obtained image data to acquire the internal spatial position information of the organ when using 4D ultrasound technology can be solved, achieving automatic analysis of the image data to acquire the spatial position information, and improving the accuracy of the acquired spatial position information.

The technical solution of the embodiments of the present disclosure may be implemented as follows.

An ultrasound image acquisition method, applied to an ultrasound image acquisition system may comprise:
  according to a received first acquisition instruction used for scanning an object to be detected, determining the operating mode of the ultrasound image acquisition system to be a first mode in which a three-dimensional image is acquired;
  transmitting first ultrasonic waves to the inside of the object to be detected in the first mode;
  receiving first ultrasonic echoes which is returned from the inside of the object to be detected and based on the first ultrasonic waves to acquire first ultrasonic echo signals, and performing beamforming on the first ultrasonic echo signals to acquire a plurality of first basic ultrasound images;
  acquiring a first reference direction and a contour of a reference sub-object to be detected according to the plurality of first basic ultrasound images;
  acquiring first spatial position information inside the object to be detected according to the first reference direction and the contour of the reference sub-object to be detected;
  generating a three-dimensional ultrasound image and/or a first planar ultrasound image of the inside of the object to be detected according to the first spatial position information inside the object to be detected; and
  displaying the three-dimensional ultrasound image and/or the first planar ultrasound image, and displaying the first spatial position information in the form of a graphical interface.

An ultrasound image acquisition method provided in an embodiment of the present disclosure and applied to an ultrasound image acquisition system may comprise:
  according to a received first acquisition instruction used for scanning an object to be detected, setting the operating mode of the ultrasound image acquisition system to be a first mode in which a three-dimensional image is acquired; and
  acquiring first spatial position information inside the object to be detected in the first mode.

In the above solution, after the step of acquiring first spatial position information inside the object to be detected in the first mode, the method may further comprise:
  generating a three-dimensional ultrasound image and/or a first planar ultrasound image of the inside of the object to be detected according to the first spatial position information inside the object to be detected.

An ultrasound image acquisition system provided in an embodiment of the present disclosure may at least comprise a display, a memory, a communication bus and a processor, wherein:
  the memory is configured to store an ultrasound image acquisition program;
  the communication bus is configured to realize connection and communication between the processor and the memory; and
  the processor is configured to execute the ultrasound image acquisition program stored in the memory to implement the following steps:
  according to a received first acquisition instruction used for scanning an object to be detected, setting the operating mode of the ultrasound image acquisition system to be a first mode in which a three-dimensional image is acquired; and
  acquiring first spatial position information inside the object to be detected in the first mode.

An ultrasound image acquisition system provided in an embodiment of the present disclosure may at least comprise a display, a memory, a communication bus, a processor and a probe, wherein:
  the memory is configured to store an ultrasound image acquisition program;
  the communication bus is configured to realize connection and communication between the processor and the memory; and
  the processor is configured to execute the ultrasound image acquisition program stored in the memory to implement the following steps:
  according to a received first acquisition instruction used for scanning an object to be detected, determining the operating mode of the ultrasound image acquisition system to be a first mode in which a three-dimensional image is acquired;

transmitting first ultrasonic waves to the inside of the object to be detected by the probe in the first mode, and receiving first ultrasonic echoes which is returned from the inside of the object to be detected and based on the first ultrasonic waves by the probe;

acquiring first ultrasonic echo signals and performing beamforming on the first ultrasonic echo signals to acquire a plurality of first basic ultrasound images;

acquiring a first reference direction and a contour of a reference sub-object to be detected according to the plurality of first basic ultrasound images;

acquiring first spatial position information inside the object to be detected according to the first reference direction and the contour of the reference sub-object to be detected;

generating a three-dimensional ultrasound image and/or a first planar ultrasound image of the inside of the object to be detected according to the first spatial position information inside the object to be detected; and displaying the three-dimensional ultrasound image and/or the first planar ultrasound image, and displaying the first spatial position information in the form of a graphical interface.

A computer storage medium provided in an embodiment of the present disclosure may store an ultrasound image acquisition program which realizes the steps of the ultrasound image acquisition method mentioned above when being executed by a processor.

In the ultrasound image acquisition methods, systems and computer storage medium provided by the embodiments of the present disclosure, according to a received first acquisition instruction for scanning the object to be detected, the operating mode of the ultrasound image acquisition system may be set to a first mode in which a stereoscopic spatial image may be collected, and first spatial position information inside the object to be detected may be acquired in the first mode; in this respect, the spatial position information of the inner of the object to be detected can be automatically obtained in a mode configured to collect stereoscopic spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

DETAILED DESCRIPTION

In order to make the objectives, technical solutions, and advantages of the embodiments of the present disclosure clearer, the specific technical solutions of the present disclosure will be further described in detail below in conjunction with the accompanying drawings in the embodiments of the present disclosure. The following examples are used to illustrate the present disclosure, but are not used to limit the scope thereof.

Figures 1, 2:
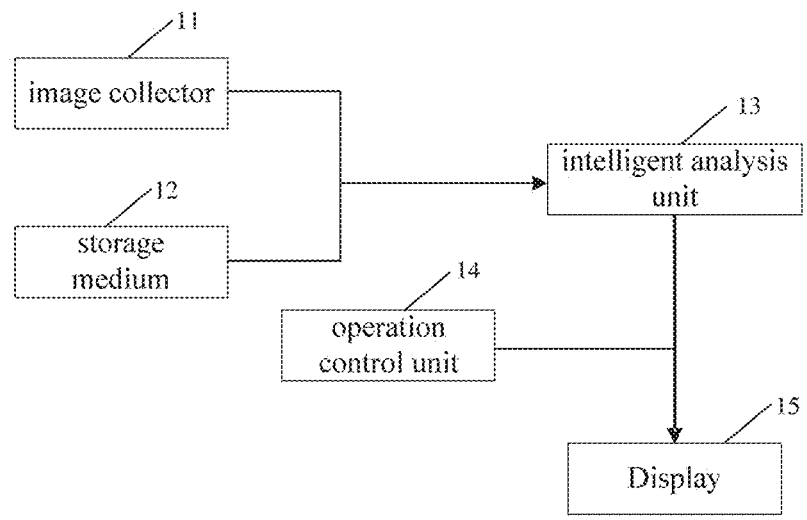
FIG. 1 is a schematically structural diagram of an ultrasound image acquisition system provided by an embodiment of the present disclosure.
FIG. 2 is a schematic flowchart of an ultrasound image acquisition method provided by an embodiment of the present disclosure.

Before introducing ultrasound image acquisition methods provided by the embodiments of the present disclosure, a brief description of ultrasound image acquisition systems provided in the embodiments of the present disclosure will be given first; wherein, the ultrasound image acquisition methods provided in the embodiments of the present disclosure can be applied to the ultrasound image acquisition systems. As shown in FIG. 1, an ultrasound image acquisition system may include: an image collector 11, a storage medium 12, an intelligent analysis unit 13, an operation control unit 14, and a display 15. The image collector 11 may include: a transmitting unit, a receiving unit and a beamforming unit. In an example of taking the heart as an object to be detected, the image collector may collect a basic ultrasound image and output it to the intelligent analysis unit 13, or the image collector 11 may store a collected basic ultrasound image in the storage medium 12 which may output the basic ultrasound image to the intelligent analysis unit 13; and the intelligent analysis unit 13 may analyze and acquire the spatial position information of the heart anatomical structure. In the example, the spatial position information of the heart anatomical structure may be modified or confirmed by a user via the operational control unit 14, and finally a required target image may be acquired according to the spatial position information and shown on the display 15 for the operator to view. Of course, it is also possible to analyze and measure the heart according to the spatial position information, or a new scan (for example, two-dimensional or multi-plane scan) may be performed by using the spatial position information. It should be noted that the basic ultrasound image may be acquired by transmitting ultrasonic waves to the inside of the heart via the transmitting unit, receiving returned echo signals via the receiving unit and performing signal processing by such as the beamforming unit.

As shown in FIG. 2, an ultrasound image acquisition method provided in an embodiment of the present disclosure may include the following steps.

Step 201: setting the operating mode of the ultrasound image acquisition system to be a first mode according to a received first acquisition instruction used for acquiring the object to be detected.

A three-dimensional (3D) spatial image may be collected in the first mode.

In this embodiment of the present disclosure, the step of setting the operating mode of the ultrasound image acquisition system to be a first mode according to a received first acquisition instruction for acquiring the object to be detected may be implemented by the ultrasound image acquisition system. The ultrasound image acquisition system may be any system that can acquire 3D ultrasound images of the inner of the object to be detected. In a feasible implementation, when the object to be detected includes an organ to be detected, the ultrasound image acquisition system can be a medical instrument for acquiring ultrasound images.

The first acquisition instruction may be sent to the ultrasound image acquisition system when the user needs to detect the internal structure of an object, for example, it may be generated by the user after touching the ultrasound image acquisition system. The object to be detected may be an object that needs to be detected by the user, for example, the object to be detected may be a human organ. The first mode may refer to a mode in which a spatial image with a stereoscopic effect may be acquired, for example, the first mode may include a three-dimensional (3D) mode and/or a 4D mode. The operating mode of the ultrasound image acquisition system may refer to a mode in which the internal position information of the object to be detected may be acquired by the ultrasound image acquisition system.

Step 202: acquiring first spatial position information inside the object to be detected in the first mode.

The step of acquiring first spatial position information inside the object to be detected in the first mode may be implemented by the ultrasound image acquisition system. The first spatial position information may refer to the spatial position information of the internal structure of the object to be detected, in this case the first spatial position information may be position information in 3D mode or 4D mode, and the first spatial position information may be expressed in different forms according to the mode it specifically refers to. When the first spatial position information refers to the position information in 3D mode, its representation form is a 3D representation form, for example, a 3D coordinate form; and when the first spatial position information refers to the position information in 4D mode, its representation form is a 4D representation form, for example, a matrix form. It should be noted that the first spatial position information may be acquired by analyzing an obtained first basic ultrasound image of the inner of the object to be detected.

In the ultrasound image acquisition method provided by the embodiments of the present disclosure, according to a received first acquisition instruction for acquiring the object to be detected, the operating mode of the ultrasound image acquisition system may be set to a first mode in which a 3D spatial image may be collected, and first spatial position information inside the object to be detected may be acquired in the first mode; in this respect, the spatial position information of the inner of the object to be detected can be automatically obtained in a mode configured to collect 3D spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

Figure 3:
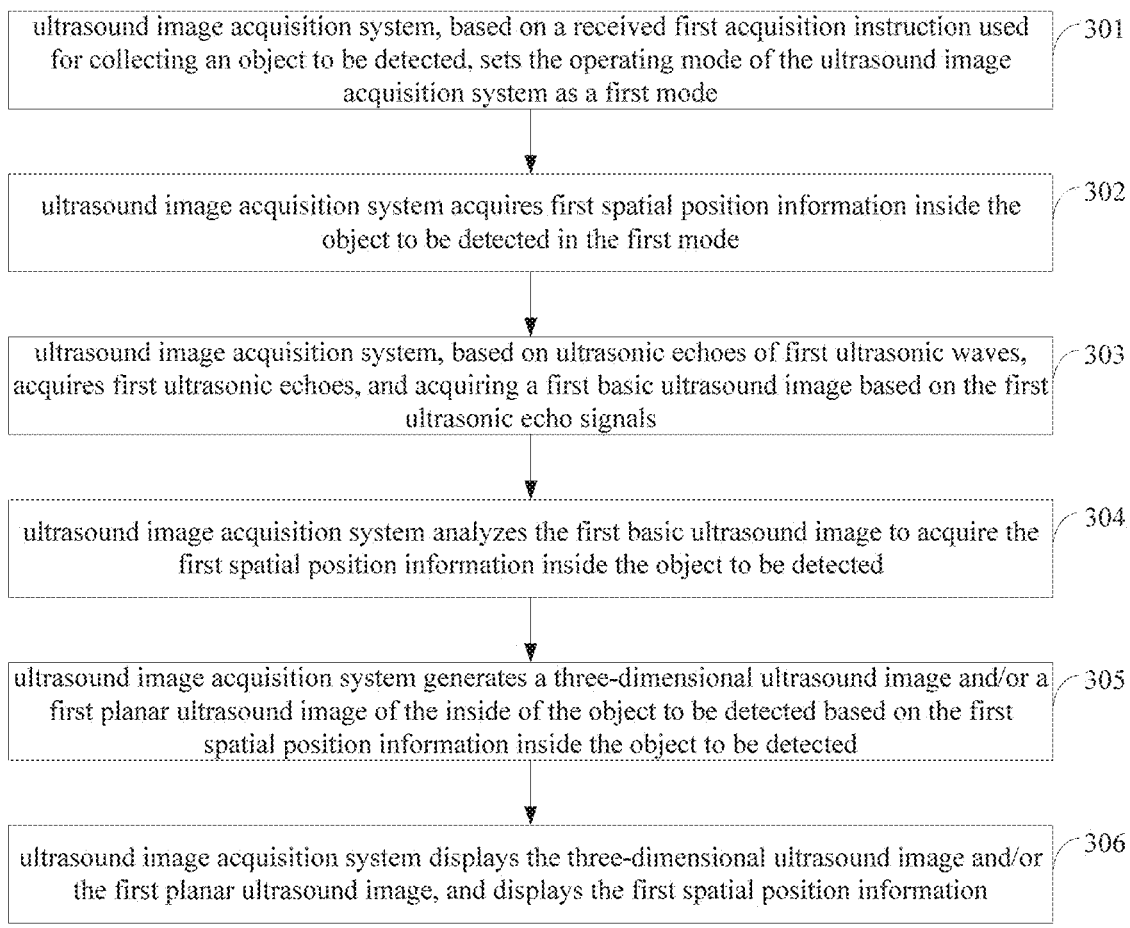
FIG. 3 is a schematic flowchart of an ultrasound image acquisition method provided by another embodiment of the present disclosure.

Based on the foregoing embodiments, as shown in FIG. 3, an ultrasound image acquisition method provided in an embodiment of the present disclosure may include the following steps.

Step 301: the ultrasound image acquisition system may set the operating mode of the ultrasound image acquisition system to be a first mode according to a received first acquisition instruction for acquiring the object to be detected.

A 3D spatial image may be collected in the first mode.

In the embodiment of the present disclosure, the setting of the operating mode of the ultrasound image acquisition system may be implemented by a processor in the ultrasound image acquisition system.

Step 302: the ultrasound image acquisition system may transmit first ultrasonic waves to the inside of the object to be detected in the first mode.

The first ultrasonic waves may be a signal that may be transmitted to the object to be detected and the echoes thereof can be received. For example, the first ultrasonic waves may include ultrasonic signals. When transmitting the ultrasonic signals, it is necessary to transmit the ultrasonic signals to the inside of the object to be detected. In a feasible implementation, an ultrasound probe may be inserted into the inside of the object to be detected to transmit the ultrasonic signals, thereby realizing the transmission of ultrasonic signals to the inside of the object to be detected.

Step 303: the ultrasound image acquisition system may acquire ultrasonic echoes of the first ultrasonic waves to get first ultrasonic echo signals, and acquires a first basic ultrasound image according to the first ultrasonic echo signals.

The first ultrasonic echo signals of the first ultrasonic waves may be signals returned by the object to be detected after receiving the first ultrasonic waves; and the first ultrasonic echo signals may be echo signals that are reflected back by the object to be detected. The basic ultrasound image may be a B-mode ultrasound image obtained by analyzing the echo signals by the beamforming unit of the ultrasound image acquisition system, and the first basic ultrasound image may be collected by the image collector 11.

Step 304: the ultrasound image acquisition system may analyze the first basic ultrasound image and acquires first spatial position information inside the object to be detected.

Step 304 may be implemented in the following manner:
analyzing the first basic ultrasound image and acquiring the first spatial position information of a sub-object to be detected included in the object to be detected in the internal space of the object to be detected.

The analysis of the first basic ultrasound image may be performed by the intelligent analysis unit 13. In an example of taking the heart as an object to be detected, the intelligent analysis unit 13 may acquire the stored first basic ultrasound image (i.e. B-mode ultrasound image), and analyze the acquired B-mode ultrasound image to gain the spatial position information of the anatomical internal structure of the heart, that is, the spatial position of various organs included in the heart. The sub-object to be detected may be organs including: ventricles, atria, mitral valve and outflow tract of left ventricle.

Step 305: the ultrasound image acquisition system may generate a first 3D ultrasound image and/or a first planar ultrasound image of the inside of the object to be detected according to the first spatial position information inside the object to be detected.

After acquiring the first spatial position information of the internal structure of the object to be detected, the first 3D ultrasound image about the inside of the object to be detected may be generated according to the spatial position information corresponding to each structure in the internal structure of the object to be detected. It should be noted that the first 3D ultrasound image may include one image or a plurality of images.

Step 306: the ultrasound image acquisition system may display the first 3D ultrasound image and/or the first planar ultrasound image, and display the first spatial position information.

The first 3D ultrasound image may include a normal view, or the first 3D ultrasound image may also include other views that mark a certain organ. The first planar ultrasound image may include a multi-plane or a single-planar view. For example, the object to be detected may include a heart, and the first three-dimensional view may include apical four-chamber (A4C), apical two-chamber (A2C), apical long axis (ALAX) views.

When displaying the first spatial position information, it may be shown on the display 15 in a variety of forms that can inform the user of the first spatial position information inside the object to be detected. For example, the first spatial position information may be displayed in a graphical user interface form, a text prompt form, or a matrix form.

It should be noted that, for the description of the same steps and the same content in this embodiment as those in other embodiments, reference may be made to the description in other embodiments, which will not be repeated here.

In the ultrasound image acquisition method provided by the embodiments of the present disclosure, according to a received first acquisition instruction for acquiring the object to be detected, the operating mode of the ultrasound image acquisition system may be set to a first mode in which a 3D spatial image may be collected, and first spatial position information inside the object to be detected may be acquired in the first mode; in this respect, the spatial position information of the inner of the object to be detected can be automatically obtained in a mode configured to collect 3D spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

Figure 4:
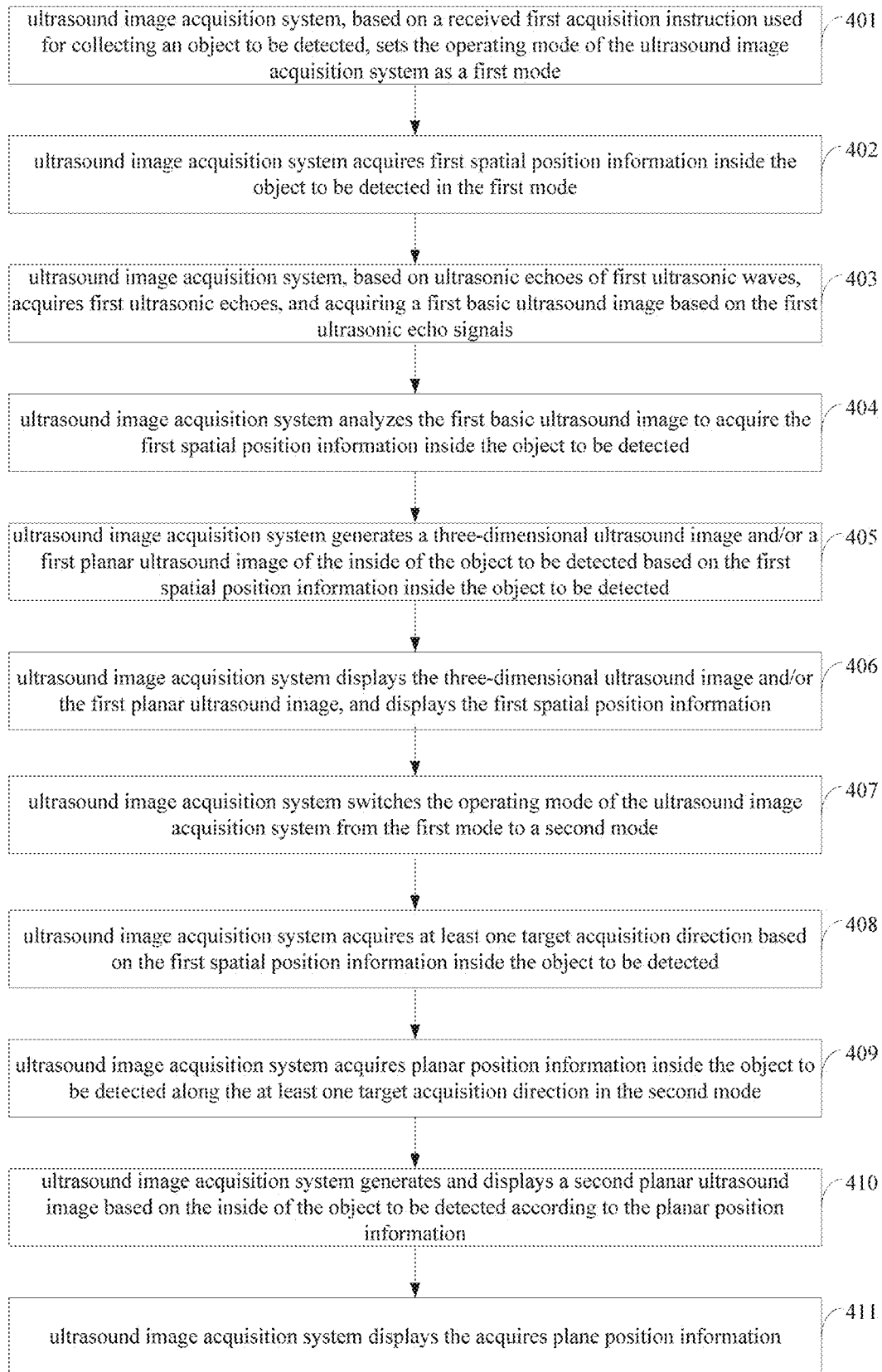
FIG. 4 is a schematic flowchart of an ultrasound image acquisition method provided by still another embodiment of the present disclosure.

Based on the foregoing embodiments, as shown in FIG. 4, an ultrasound image acquisition method provided in an embodiment of the present disclosure may include the following steps.

Step 401: the ultrasound image acquisition system may set the operating mode of the ultrasound image acquisition system to be a first mode according to a received first acquisition instruction for acquiring the object to be detected.

A stereoscopic spatial image may be collected in the first mode.

Step 402: the ultrasound image acquisition system may transmit first ultrasonic waves to the inside of the object to be detected in the first mode.

Step 403: the ultrasound image acquisition system acquires first ultrasonic echoes of the first ultrasonic waves to get first ultrasonic echo signals, and acquires a first basic ultrasound image according to the first ultrasonic echo signals.

Step 404: the ultrasound image acquisition system may analyze the first basic ultrasound image and acquire first spatial position information inside the object to be detected.

Step 404 may be implemented in the following manner:
analyzing the first basic ultrasound image and acquiring the first spatial position information of a sub-object to be detected included in the object to be detected in the internal space of the object to be detected.

Step 405: the ultrasound image acquisition system may generate a first 3D ultrasound image and/or a first planar ultrasound image of the inside of the object to be detected according to the first spatial position information inside the object to be detected.

Step 406: the ultrasound image acquisition system may display the first 3D ultrasound image and/or the first planar ultrasound image, and display the first spatial position information.

The generated first 3D ultrasound image may be shown on the display 15. In a feasible implementation, the display 15 may be a touch screen with a touch function or a display screen without a touch function.

Figure 5:
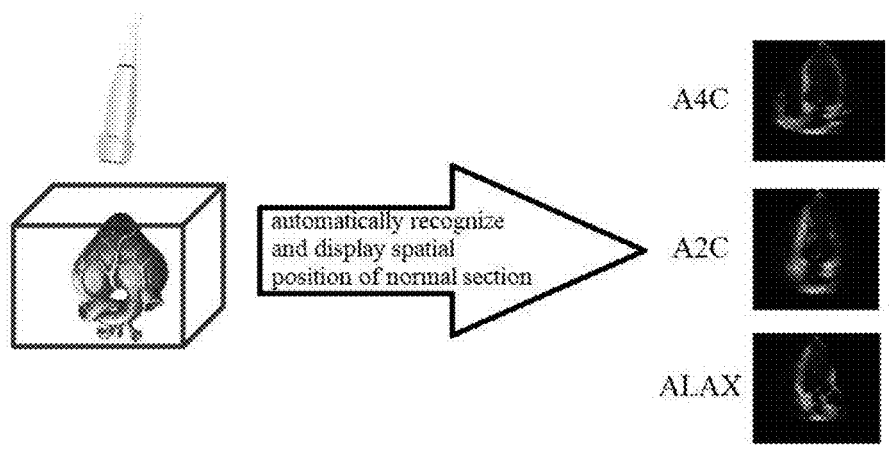
FIG. 5 is a schematic diagram of acquiring a three-dimensional ultrasound image through an ultrasound image acquisition method according to an embodiment of the present disclosure.

In an example of taking the heart as an object to be detected, the first 3D ultrasound image including apical four-chamber (A4C), apical two-chamber (A2C), apical long axis (ALAX) views and the first mode being 3D/4D mode, as shown in FIG. 5, after transmitting ultrasonic wave to the heart by the ultrasound probe, the normal views of A4C, A2C and ALAX of the heart may finally obtained after analysis.

Step 407: the ultrasound image acquisition system may switch the operating mode of the ultrasound image acquisition system from the first mode to a second mode.

A planar image can be collected in the second mode.

In other embodiments of the present disclosure, the second mode may refer to a mode in which a planar image can be acquired. For example, the second mode may include a two-dimensional (2D) mode and/or a multi-plane mode. Moreover, the switching of the operating mode of the ultrasound image acquisition system, that is, the switching of the operating mode from the first mode to the second mode, may be implemented by the processor in the ultrasound image acquisition system.

Step 408: the ultrasound image acquisition system may acquire at least one target acquisition direction according to the first spatial position information inside the object to be detected.

The target acquisition direction may be obtained by the ultrasound image acquisition system automatically analyzing the first spatial position information in the first mode; of course, the target acquisition direction may also be jointly obtained according to a certain organ indicated by a second acquisition instruction and the first spatial position information, where the second acquisition instruction inputted by the user for collecting planar images of the organ may be received by the processor of the ultrasound image acquisition system. That is, the target acquisition direction may be determined automatically by the ultrasound image acquisition system, or it may be determined according to the user's instruction.

Step 409: the ultrasound image acquisition system may acquire planar position information inside the object to be detected along at least one target acquisition direction in the second mode.

The target acquisition direction determined by the processor in the ultrasound image acquisition system may include one or more directions, which means that the ultrasound probe may transmit ultrasonic waves from one direction based on one plane, or from multiple directions based on multiple planes. Moreover, the position information of the internal structure of the heart obtained in the second mode may be two-dimensional position information, which may refer to planar position information.

Step 410: the ultrasound image acquisition system may generate and display a second planar ultrasound image of the inside of the object to be detected according to the planar position information.

Figure 7:
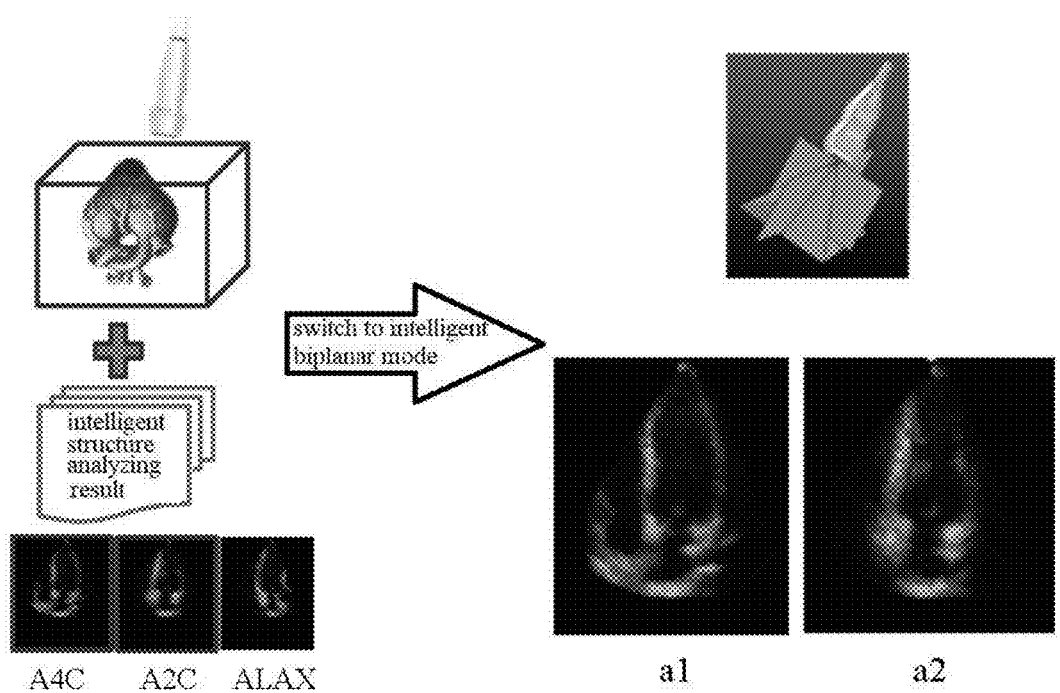
FIG. 7 is a schematic diagram of acquiring a three-dimensional ultrasound image and a planar ultrasound image through an ultrasound image acquisition method according to an embodiment of the present disclosure.

The specific process of generating and displaying the second planar ultrasound image of the inside of the object to be detected according to the planar position information, similar to the aforesaid process of generating the 3D ultrasound image of the inside of the object to be detected according to the first spatial position information, may be described with reference to the description in the foregoing embodiments, which will not be repeated here. In an example of taking the heart as an object to be detected, the first 3D ultrasound image including apical four-chamber (A4C), apical two-chamber (A2C), apical long axis (ALAX) views, the first mode being 3D/4D mode, the second mode being multi-plane mode and the second planar ultrasound image including a four-chamber plan view and a two-chamber plan view of the heart, as shown in FIG. 7, in 3D/4D mode, the normal views of A4C, A2C and ALAX of the heart shown in FIG. 7 can finally be obtained according to intelligent analysis after using the ultrasound probe to transmit ultrasonic waves to the inside of the heart; and then in the multi-plane mode, the direction of the plan view corresponding to A4C and A2C may be determined according to the volume data (first spatial position information) obtained in 3D/4D mode, the ultrasonic waves may be transmitted to the inside of the heart in the corresponding direction via the probe to acquire views a1, a2 in FIG. 7 to display on the display 15. The view a1 may refer to the plan view of A4C, and the view a2 may refer to the plan view of A2C.

In addition, the data required by 4D ultrasound technology needs to balance spatial resolution and temporal resolution; for example, for the heart, a larger acquisition range (complete left ventricle) and a higher frame rate are required for measurement such as ejection fraction and myocardial strain. With the ultrasound image acquisition methods provided in the embodiments of the present disclosure, ultrasound images can be acquired in 3D/4D mode, or in 2D mode and/or multi-plane mode, while satisfying the requirements for spatial resolution and time resolution.

Step 411: the ultrasound image acquisition system may display the acquired planar position information.

Figure 6:
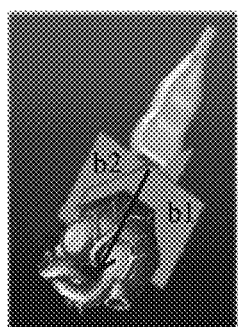
FIG. 6 is a schematic diagram of showing acquired planar position information in a graphical manner according to an embodiment of the present disclosure.

When displaying the planar position information corresponding to the target acquisition direction, it may be shown on the display 15 in a variety of forms that can inform the user of the planar position information corresponding to the target acquisition direction. For example, the planar position information may be displayed in a graphical user interface form, a text prompt form, or a matrix form. For example, when the object to be detected is the heart, the target acquisition direction may include two directions, and the planar position information corresponding to the target acquisition direction may include plane b1 and plane b2. The manner shown in FIG. 6 is to display the planar position information in the graphical form; In this respect, the ultrasound probe may transmit ultrasonic waves according to the plane b1 and the plane b2 inside the heart, and the plane b1 and the plane b2 may be displayed on a diagram having the heart.

It should be noted that, for the description of the same steps and the same content in this embodiment as those in other embodiments, reference may be made to the description in other embodiments, which will not be repeated here.

Based on the foregoing embodiments, the method in other embodiments of the present disclosure may further include the following steps.

A: the ultrasound image acquisition system may display the first spatial position information inside the object to be detected, and receives a modification operation according to the first spatial position information inside the object to be detected.

B: the ultrasound image acquisition system may modify the first spatial position information inside the object to be detected according to the modification operation, and displays the modified first spatial position information inside the object to be detected.

After obtaining the first spatial position information, the first spatial position information may be modified by the user, and then the first 3D ultrasound image may be generated according to the modified first spatial position information. It should be noted that the modification of the first spatial position information may be realized by operating the operational control unit 14. Of course, the planar position information generated in the second mode may also be modified by the user via the operational control unit, and then the second planar ultrasound image may be generated according to the modified planar position information.

Correspondingly, step 405 can be implemented in the following manner:
  generating the first 3D ultrasound image and/or the first planar ultrasound image of the inside of the object to be detected according to the modified first spatial position information inside the object to be detected.

Correspondingly, step 409 can be implemented in the following manner:
  determining at least one target acquisition direction according to the modified first spatial position information inside the object to be detected and identification information.

According to the generated spatial position information which may be modified subsequently, the target acquisition direction when acquiring the second planar ultrasound image may be determined by the user operating the operational control unit.

Based on the foregoing embodiment, the method in other embodiments of the present disclosure may further include the following steps.

C: the ultrasound image acquisition system may detect and analyze the object to be detected according to the first spatial position information inside the object to be detected.

D: the ultrasound image acquisition system may detect and analyze the object to be detected according to the planar position information inside the object to be detected along at least one target acquisition direction.

The detection analysis in this embodiment may include echocardiographic measurement, for example, cardiac function measured by using bi-plane of A4C and A2C (ejection fraction value measurement) or myocardial motion analyzed by using three planes of A4C, A2C and ALAX.

In the ultrasound image acquisition method provided by the embodiments of the present disclosure, according to a received first acquisition instruction for acquiring the object to be detected, the operating mode of the ultrasound image acquisition system may be set to a first mode in which a stereoscopic spatial image may be collected, and first spatial position information inside the object to be detected may be acquired in the first mode; in this respect, the spatial position information of the inner of the object to be detected can be automatically obtained in a mode configured to collect stereoscopic spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

Figure 8:
FIG. 8 is a schematic diagram of an implementation process of an ultrasound image acquisition method provided by another embodiment of the present disclosure.

Based on the foregoing embodiments, as shown in FIG. 8, an ultrasound image acquisition method provided in an embodiment of the present disclosure may include the following steps.

Step 501: the ultrasound image acquisition system may set the operating mode of the ultrasound image acquisition system to be a first mode according to a received first acquisition instruction for acquiring the object to be detected.

A stereoscopic spatial image may be collected in the first mode.

Step 502: the ultrasound image acquisition system may transmit first ultrasonic waves to the inside of the object to be detected in the first mode.

Step 503: the ultrasound image acquisition system may acquire first ultrasonic echoes of the first ultrasonic waves to get first ultrasonic echo signals, and acquires a first basic ultrasound image according to the first ultrasonic echo signals.

Step 504: the ultrasound image acquisition system may analyze the first basic ultrasound image and acquire first spatial position information inside the object to be detected.

Step 504 may be implemented in the following manner: analyzing the first basic ultrasound image and acquiring the first spatial position information of a sub-object to be detected included in the object to be detected in the internal space of the object to be detected.

Step 505: the ultrasound image acquisition system may generate a first 3D ultrasound image and/or a first planar ultrasound image of the inside of the object to be detected according to the first spatial position information inside the object to be detected.

Step 506: the ultrasound image acquisition system may display the first 3D ultrasound image and/or the first planar ultrasound image, and display the first spatial position information.

Step 507: the ultrasound image acquisition system may switch the operating mode of the ultrasound image acquisition system from the first mode to a second mode.

A planar image can be collected in the second mode.

Step 508: the ultrasound image acquisition system may receive a second acquisition instruction used for acquiring a planar image of the inside of the object to be detected.

The second collection instruction may carry identification information of the sub-object to be detected.

Figure 9:
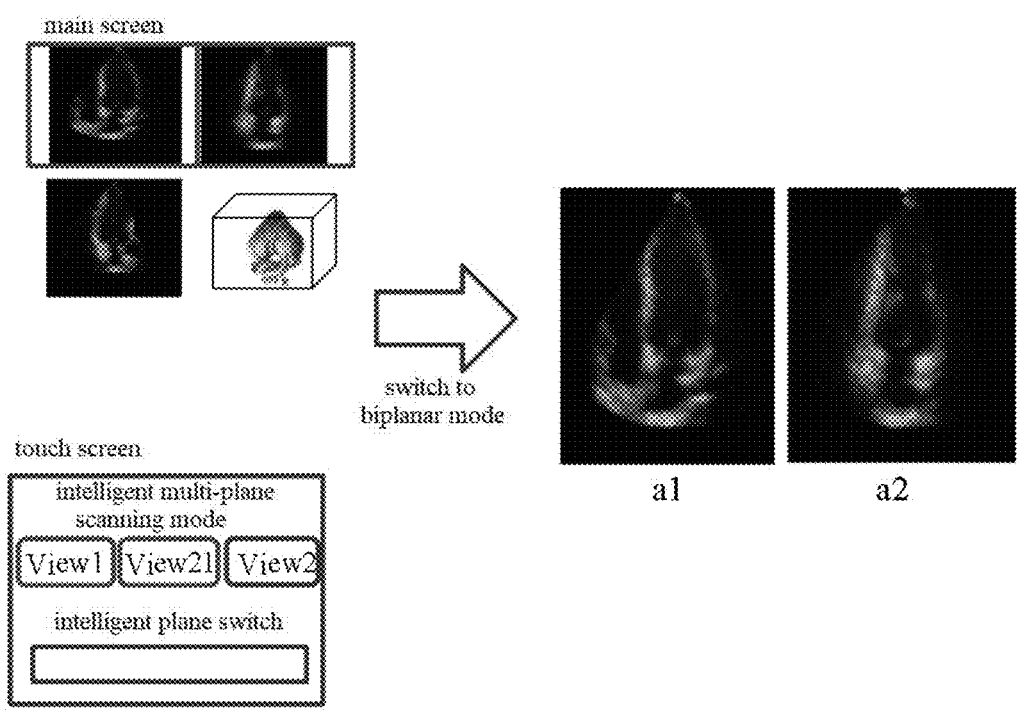
FIG. 9 is a schematic diagram of acquiring a three-dimensional ultrasound image and a planar ultrasound image through an ultrasound image acquisition method according to another embodiment of the present disclosure.

In other embodiments of the present disclosure, when the object to be detected is the heart, the identification information of the sub-object to be detected may refer to the identification information of organs included in the heart (such as ventricles, atria, mitral valve, outflow tract of left ventricle, etc.) or the views (such as A4C, A2C, etc.). However, the identification information may be sent by the user to the ultrasound image acquisition system via the display. Moreover, the identification information may be information used to uniquely identify the organ in the heart that the user wants to acquire. As shown in FIG. 9, when the display is a touch screen, the users can select a specific view they want to view via the touch screen. For example, View1 represents A4C, View2 represents A2C, and View3 represents ALAX; after the user touches the buttons corresponding to View1 and View2; the ultrasound image acquisition system may be switched to a biplanar mode, and views a1, a2 may finally be shown on the display screen, as shown in FIG. 9.

Step 509: the ultrasound image acquisition system may determine at least one target acquisition direction according to the identification information and the first spatial position information inside the object to be detected.

The ultrasound image acquisition system may automatically determine at least one target acquisition direction according to the organs to be viewed given by the user and the first spatial position information obtained in the first mode. As shown in FIG. 9, the automatically determined target acquisition direction may be two, and the corresponding planes may be the planes where views a1, a2 are located.

Step 510: the ultrasound image acquisition system may transmit second ultrasonic waves to the inside of the object to be detected along at least one target acquisition direction in the second mode.

The second ultrasonic waves may be a signal that may be transmitted to the object to be detected and received as a return signal. When transmitting the ultrasonic signals, it is necessary to transmit the ultrasonic signals to the inside of the object to be detected. In a feasible implementation, an ultrasound probe may be inserted into the inside of the object to be detected to transmit the ultrasonic signals, thereby realizing the transmission of ultrasonic signals to the inside of the object to be detected. The second ultrasonic waves may be the same as or different from the first ultrasonic waves, but the transmission mode of the second ultrasonic waves is different from that of the first ultrasonic waves.

Step 511: the ultrasound image acquisition system may acquire second ultrasonic echoes of the second ultrasonic waves to gain second ultrasonic echo signals.

The second ultrasonic echo signals may be signals returned by the object to be detected after receiving the second ultrasonic waves; and the second ultrasonic echo signals may be echo signals of the ultrasonic waves that are reflected back by the object to be detected.

Step 512: the ultrasound image acquisition system may acquire planar position information inside the object to be detected along at least one target acquisition direction according to the second ultrasonic echo signals.

Step 513: the ultrasound image acquisition system may generate and displays a second planar ultrasound image of the inside of the object to be detected according to the planar position information.

After the processor generates the second planar ultrasound image of the inside of the object to be detected, the second planar ultrasound image may be shown on the display 15.

Step 514: the ultrasound image acquisition system may display the planar position information.

Based on the foregoing embodiments, the following steps may be performed after step 505 in other embodiments of the present application.

Step 515: the ultrasound image acquisition system may store the first spatial location information inside the object to be detected.

The first spatial position information inside the heart obtained in the first mode may be stored in storage medium 12 for subsequent use in the ultrasound scan of the heart.

Based on the foregoing embodiments, the following steps may be performed after step 515 in other embodiments of the present application.

Step 516: the ultrasound image acquisition system may acquire the first spatial position information inside the object to be detected stored in the ultrasound image acquisition system according to a received third acquisition instruction used for scanning the object to be detected.

Step 516 may be implemented in the following manner:

According to the received third acquisition instruction used for scanning the object to be detected, the first spatial position information inside the object to be detected stored in the ultrasound image acquisition system and the second basic ultrasound image of the inside of the object to be detected may be acquired.

Step 517: according to the stored first spatial position information inside the object to be detected, the ultrasound image acquisition system may acquire second spatial position information inside the object to be detected according to the third acquisition instruction.

Step 517 may be implemented in the following manner:

According to the stored first spatial position information inside the object to be detected and the second basic ultrasound image, the second spatial position information inside the object to be detected may be acquired according to the third acquisition instruction.

Step 518: the ultrasound image acquisition system may generate and displays a second 3D ultrasound image of the inside of the object to be detected according to the second spatial position information inside the object to be detected.

After one ultrasound scan in the first mode, the ultrasound image acquisition system may, when receiving the second acquisition instruction to perform another ultrasound scan in the first mode, first acquire the spatial position information of the object to be detected stored after the previous scan, then perform a modification on the spatial position information acquired from the previous scan (first spatial position information) via the operational control unit 14 of the ultrasound image acquisition system to gain a new spatial position information corresponding to the result of current scan (i.e. second spatial position information), and generate the second 3D ultrasound image of the inside of the object to be detected according to the second spatial position information according to the way in which the first 3D ultrasound image is generated according to the first spatial position information.

It should be noted that, for the description of the same steps and the same content in this embodiment as those in other embodiments, reference may be made to the description in other embodiments, which will not be repeated here.

In the ultrasound image acquisition method provided by the embodiments of the present disclosure, according to a received first acquisition instruction for acquiring the object to be detected, the operating mode of the ultrasound image acquisition system may be set to a first mode in which a stereoscopic spatial image may be collected, and first spatial position information inside the object to be detected may be acquired in the first mode; in this respect, the spatial position information of the inner of the object to be detected can be automatically obtained in a mode configured to collect stereoscopic spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

Based on the foregoing embodiment, the method in other embodiments of the present disclosure may further include the following steps.

A: the ultrasound image acquisition system may display the first spatial position information inside the object to be detected, and receive a modification operation according to the first spatial position information inside the object to be detected.

B: the ultrasound image acquisition system may modify the first spatial position information inside the object to be detected according to the modification operation, and display the modified first spatial position information inside the object to be detected.

After obtaining the first spatial position information, the first spatial position information may be modified by the user, and then the first 3D ultrasound image may be generated according to the modified first spatial position information. It should be noted that the modification of the first spatial position information may be realized by operating the operational control unit 14. Of course, the planar position information generated in the second mode may also be modified by the user via the operational control unit, and then the second planar ultrasound image may be generated according to the modified planar position information.

Figure 10:
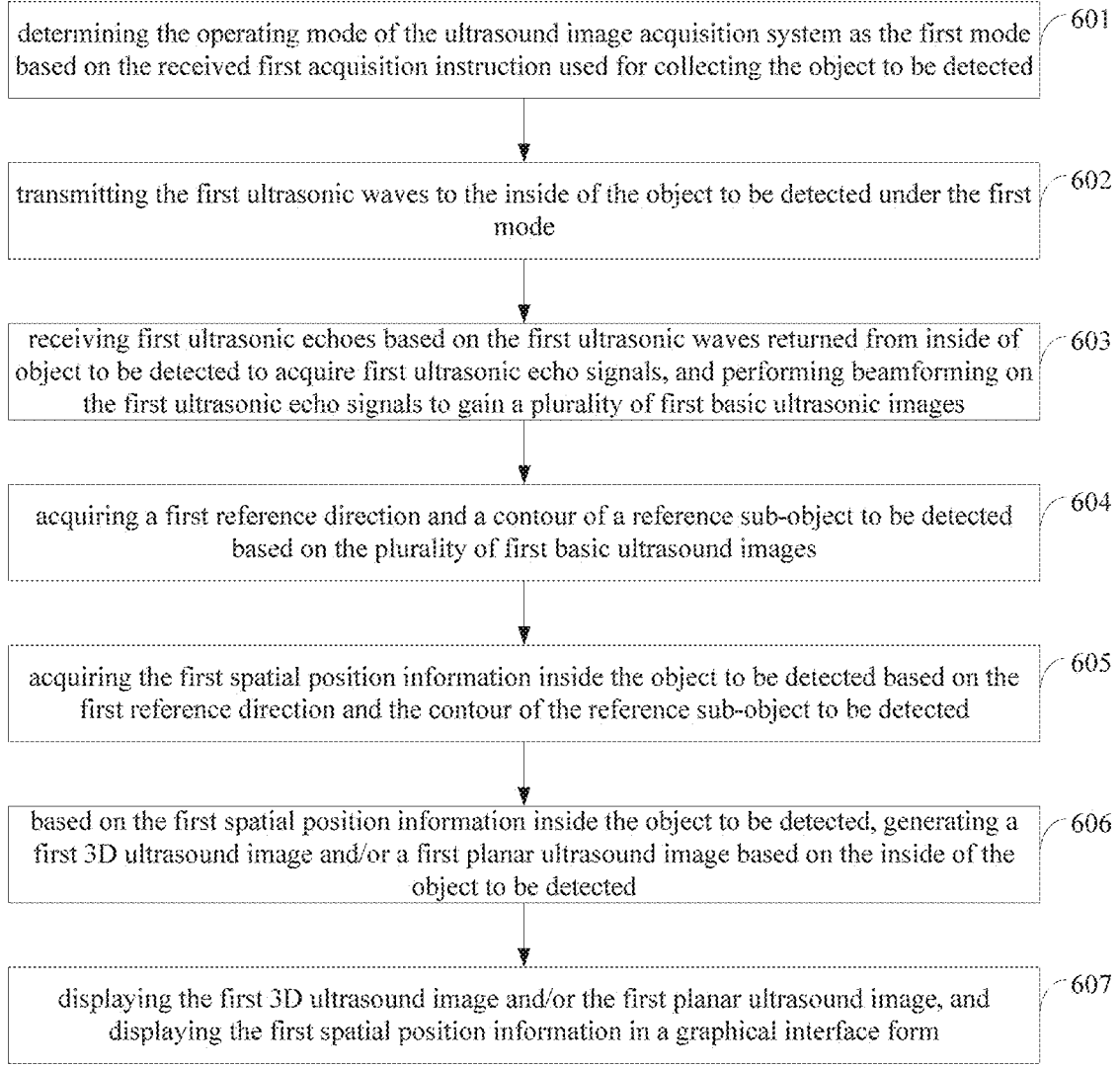
FIG. 10 is a schematic diagram of an implementation process of an ultrasound image acquisition method provided by another embodiment of the present disclosure.

Based on the foregoing embodiments, as shown in FIG. 10, an ultrasound image acquisition method applied to an ultrasound image acquisition system and provided in an embodiment of the present disclosure may include the following steps.

Step 601: determining the operating mode of the ultrasound image acquisition system to be the first mode according to the received first acquisition instruction used for scanning the object to be detected.

A stereoscopic spatial image may be collected in the first mode.

Step 602: transmitting the first ultrasonic waves to the inside of the object to be detected under the first mode.

The first ultrasonic waves may be transmitted to the inside of the object to be detected via the probe.

Step 603: receiving first ultrasonic echoes of the first ultrasonic waves returned from the inside of the object to be detected to acquire first ultrasonic echo signals, and performing beamforming on the first ultrasonic echo signals to gain a plurality of first basic ultrasonic images.

The step of performing beamforming on the first ultrasonic echo signals may be realized by the beamforming unit of the ultrasound image acquisition system.

Step 604: acquiring a first reference direction and a contour of a reference sub-object to be detected according to the plurality of first basic ultrasound images.

The first reference direction and the reference sub-object to be detected may be determined according to a specific object referred to by the object to be detected in practice. When the object to be detected includes the heart, the first reference direction may be the direction of long axis of the heart, and the reference sub-object to be detected may refer to the left ventricle inside the heart.

Step 605: acquiring the first spatial position information inside the object to be detected according to the first reference direction and the contour of the reference sub-object to be detected.

The first basic ultrasound image may be processed according to the first reference direction, and then the first spatial position information inside the object to be detected may be acquired according to the reference sub-object to be detected and the processed first basic ultrasound image.

Step 606: according to the first spatial position information inside the object to be detected, generating a first 3D ultrasound image and/or a first planar ultrasound image of the inside of the object to be detected.

Step 607: displaying the first 3D ultrasound image and/or the first planar ultrasound image, and displaying the first spatial position information in a graphical interface form.

It should be noted that, for the description of the same steps and the same content in this embodiment as those in other embodiments, reference may be made to the description in other embodiments, which will not be repeated here.

In the ultrasound image acquisition method provided by the embodiments of the present disclosure, the spatial position information of the inner of the object to be detected can be automatically obtained in a mode configured to collect stereoscopic spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

Figure 11:
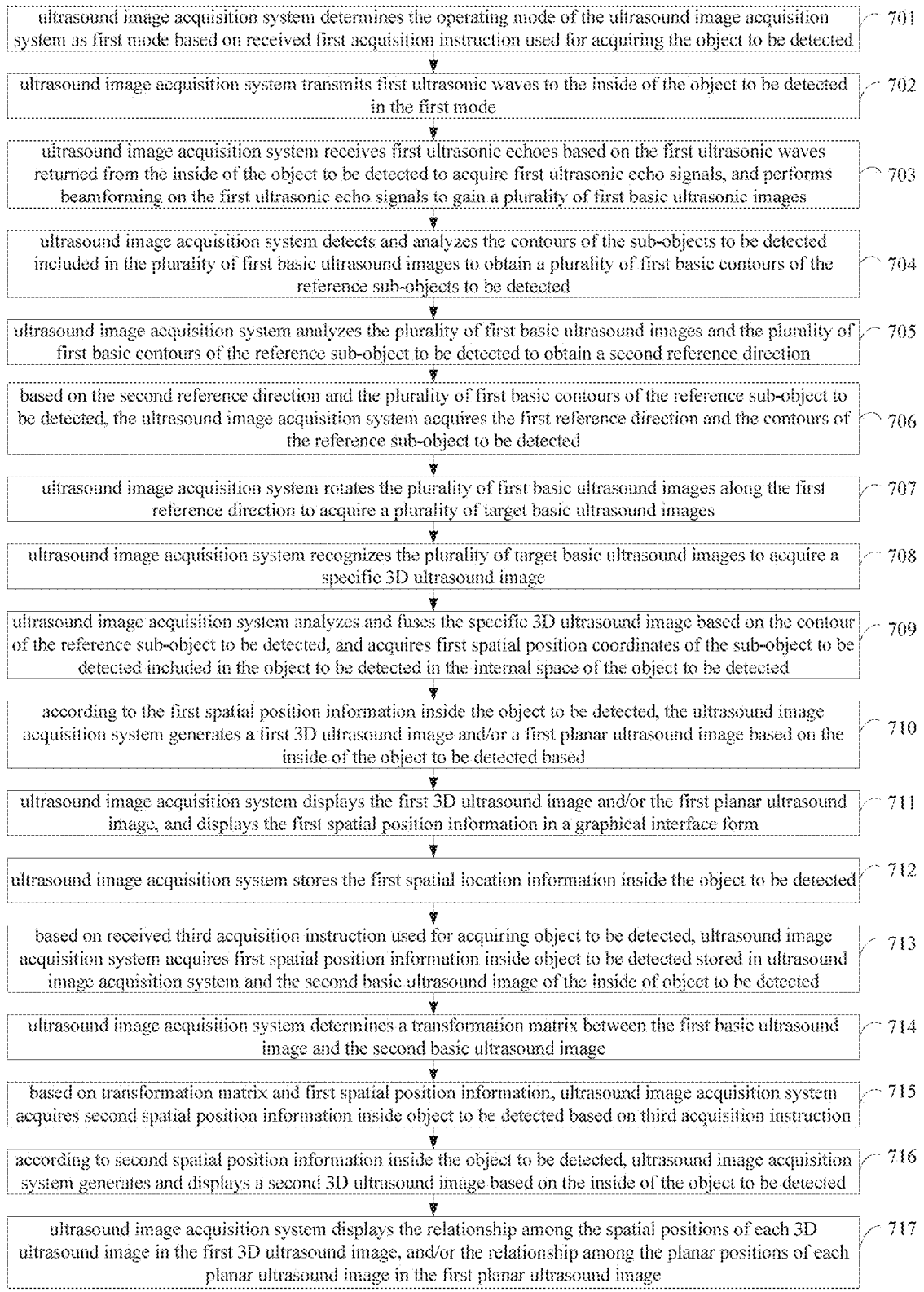
FIG. 11 is a schematic diagram of an implementation process of an ultrasound image acquisition method provided by still another embodiment of the present disclosure.

Based on the foregoing embodiments, as shown in FIG. 11, an ultrasound image acquisition method provided in an embodiment of the present disclosure may include the following steps.

Step 701: the ultrasound image acquisition system may determine the operating mode of the ultrasound image acquisition system to be a first mode according to a received first acquisition instruction used for acquiring the object to be detected.

A stereoscopic spatial image may be collected in the first mode.

Step 702: the ultrasound image acquisition system may transmit first ultrasonic waves to the inside of the object to be detected in the first mode.

Step 703: the ultrasound image acquisition system may receive first ultrasonic echoes of the first ultrasonic waves returned from the inside of the object to be detected to acquire first ultrasonic echo signals, and perform beamforming on the first ultrasonic echo signals to gain a plurality of first basic ultrasonic images.

Step 704: the ultrasound image acquisition system may detect and analyze the contours of the sub-objects to be detected included in the plurality of first basic ultrasound images to obtain a plurality of first basic contours of the reference sub-objects to be detected.

When the first basic ultrasound images include B-mode ultrasound images, the ultrasound image acquisition system may analyze the sub-objects to be detected in each B-mode ultrasound image to gain the contours of the sub-objects to be detected included in each B-mode ultrasound image, and acquire the contours of the reference sub-objects to be detected according to the contours of the sub-objects to be detected, thereby acquiring the plurality of first basic contours.

Step 705: the ultrasound image acquisition system may analyze the plurality of first basic ultrasound images and the plurality of first basic contours of the reference sub-object to be detected to obtain a second reference direction.

By analyzing the plurality of first basic contours, and according to the analysis result and the relationship between the first basic ultrasound image and each first basic contour of the reference sub-object to be detected, the second reference direction of the sub-object to be detected may be determined.

Step 706: according to the second reference direction and the plurality of first basic contours of the reference sub-object to be detected, the ultrasound image acquisition system may acquire the first reference direction and the contours of the reference sub-object to be detected.

Step 706 may be implemented in the following manner:

Step a: the ultrasound image acquisition system may synthesize a plurality of first basic contours of the reference sub-object to be detected to acquire a second basic contour of the reference sub-object to be detected.

The second basic contour is obtained by synthesizing the plurality of first basic contours of the reference sub-object to be detected.

Step b: according to the second basic contour of the reference sub-object to be detected and the second reference direction, the ultrasound image acquisition system may analyze the plurality of first basic ultrasound images to acquire the basic position of the sub-object to be detected included in the object to be detected.

When the object to be detected is the heart, the sub-objects to be detected may include organs such as the apex, annulus, atrium, left ventricle, and right ventricle. In a feasible implementation, according to the second basic contour of reference sub-object to be detected and the second reference direction, and combined with the relationship between the sub-objects to be detected, the plurality of first basic ultrasound images may be analyzed to acquire the basic position of the sub-objects to be detected.

Step c: the ultrasound image acquisition system may calibrate the first basic contour of the reference sub-object to be detected and the second reference direction according to the basic position of the sub-object to be detected to acquire the first reference direction and the contour of the reference sub-object to be detected.

The first reference direction may be acquired after calibrating the second reference direction, and the contour of the reference sub-object to be detected may be acquired after calibrating the first basic contour of the reference sub-object to be detected.

Step 707: the ultrasound image acquisition system may rotate the plurality of first basic ultrasound images along the first reference direction to acquire a plurality of target basic ultrasound images.

The target basic ultrasound images may be obtained by rotating the plurality of first basic ultrasound images by a certain angle; then, the target basic ultrasound images may also be B-mode ultrasound images.

Step 708: the ultrasound image acquisition system may recognize the plurality of target basic ultrasound images to acquire a specific 3D ultrasound image.

The specific 3D ultrasound image may be acquired after identifying the normal view from each target basic ultrasound image. In a feasible implementation, the specific 3D ultrasound image may be views including A4C, A2C and ALAX acquired according to the target basic ultrasound image. Of course, a plurality of views such as A4C, A2C, and ALAX may be acquired in the embodiment of the present disclosure.

Step 709: the ultrasound image acquisition system may analyze and fuse the specific 3D ultrasound image according to the contour of the reference sub-object to be detected, and acquire first spatial position coordinates of the sub-object to be detected included in the object to be detected in the internal space of the object to be detected.

The first spatial position information may include first spatial position coordinates.

It should be noted that each specific 3D ultrasound image may be identified and analyzed by the ultrasound image acquisition system according to the contours of the reference sub-objects to be detected, and the identified and analyzed images may be perform with fusion and conversion to acquire the first spatial position coordinates. In a feasible implementation, the first spatial position coordinates may be presented in matrix form.

Step 710: according to the first spatial position information inside the object to be detected, the ultrasound image acquisition system may generate a first 3D ultrasound image and/or a first planar ultrasound image of the inside of the object to be detected based.

Step 711: the ultrasound image acquisition system may display the first 3D ultrasound image and/or the first planar ultrasound image, and display the first spatial position information in a graphical interface form.

Based on the foregoing embodiment, in other embodiments of the present disclosure, the method may further include the following steps.

Step 712: the ultrasound image acquisition system may store the first spatial location information inside the object to be detected.

Step 713: according to the received third acquisition instruction used for acquiring the object to be detected, the ultrasound image acquisition system may acquire the first spatial position information inside the object to be detected stored in the ultrasound image acquisition system and the second basic ultrasound image of the inside of the object to be detected.

The second basic ultrasound image may also be a B-mode ultrasound image.

Step 714: the ultrasound image acquisition system may determine a transformation matrix between the first basic ultrasound image and the second basic ultrasound image.

The transformation matrix may be obtained after comparing and analyzing the first basic ultrasound image and the second basic ultrasound image. The transformation matrix may be a transformation matrix of spatial position between the first basic ultrasound image and the second basic ultrasound image.

Step 715: according to the transformation matrix and the first spatial position information, the ultrasound image acquisition system may acquire the second spatial position information inside the object to be detected according to the third acquisition instruction.

The second spatial position information may be obtained by multiplying the first spatial position information and the transformation matrix. Given that the transformation matrix is T, and the first spatial position information and the second spatial position information are presented in matrix form as matrix1 and matrix2 respectively, then matrix2=matrix1*T.

Step 716: according to the second spatial position information inside the object to be detected, the ultrasound image acquisition system may generate and display a second 3D ultrasound image of the inside of the object to be detected.

Step 717: the ultrasound image acquisition system may display the relationship among the spatial positions of each 3D ultrasound image in the first 3D ultrasound image, and/or the relationship among the planar positions of each planar ultrasound image in the first planar ultrasound image.

Based on the foregoing embodiment, in other embodiments of the present disclosure, step 710 may be implemented in the following manner.

According to the first spatial position information inside the object to be detected, the first 3D ultrasound image and/or the first planar ultrasound image of the inside of the object to be detected may be generated according to the first ultrasound echo signal.

Alternately, according to the first spatial position information inside the object to be detected, the second ultrasonic waves may be transmitted to the inside of the object to be detected, the second ultrasonic echoes of the second ultrasonic waves returned from the inside of the object to be detected may be received to acquire the second ultrasonic echo signals, and the first 3D ultrasonic image and/or the first planar ultrasonic image of the interior of the object to be detected according to the second ultrasonic echo signals.

The second ultrasonic waves may be different from the first ultrasonic waves.

A scanning area corresponding to the first ultrasonic waves may be larger than a scanning area corresponding to the second ultrasonic waves.

In other embodiments of the present disclosure, after acquiring the first spatial position information, the ultrasound image acquisition system can acquire the first 3D ultrasound image and/or the first planar ultrasound image with high frame rate and high spatial resolution in a specific orientation according to the first spatial position information. Of course, the first 3D ultrasound image and/or the first planar ultrasound image may be obtained by transmitting ultrasonic waves to the inside of the object to be detected.

It should be noted that, for the description of the same steps and the same content in this embodiment as those in other embodiments, reference may be made to the description in other embodiments, which will not be repeated here.

Figure 12:
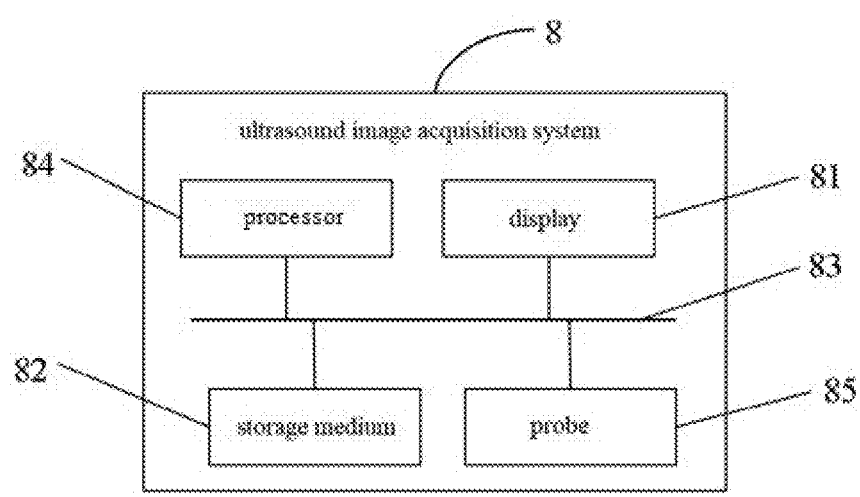
FIG. 12 is a schematically structural diagram of an ultrasound image acquisition system provided by an embodiment of the present disclosure.

Based on the foregoing embodiment, an ultrasound image acquisition system, which may be applied to the ultrasound image acquisition methods corresponding to the embodiments shown in FIGS. 2-4, may be provided in the embodiment of the present disclosure provides. Referring to FIG. 12, the ultrasound image acquisition system 8 may at least include: a display 81, a memory 82, a communication bus 83 and a processor 84.

The memory 82 may be configured to store an ultrasound image acquisition program;

The communication bus 83 may be configured to realize connection and communication between the processor 84 and the memory 82;

The processor 84 may be configured to execute the ultrasound image acquisition program stored in the memory 82 to implement the following steps:

according to a received first acquisition instruction used for scanning an object to be detected, setting the operating mode of the ultrasound image acquisition system to be a first mode in which a three-dimensional image is acquired; and acquiring first spatial position information inside the object to be detected in the first mode.

In the ultrasound image acquisition system provided by the embodiments of the present disclosure, the spatial position information of the inner of the object to be detected can be obtained in a mode configured to collect 3D spatial images, solving a problem that only image data can be acquired without the internal spatial position information when using 4D ultrasound technology, and ensuring the comprehensiveness and accuracy of the obtained data.

In other embodiments of the present disclosure, the processor 84 may be configured to execute the ultrasound image acquisition program stored in the memory 82 to further implement the following steps:

generating a three-dimensional ultrasound image and/or a first planar ultrasound image of the inside of the object to be detected according to the first spatial position information inside the object to be detected.

In other embodiments of the present disclosure, the processor 84 may be configured to execute the ultrasound image acquisition program stored in the memory 82 to further implement the following steps:

displaying the three-dimensional ultrasound image and/or the first planar ultrasound image and displaying the first spatial position information on the display 81.

In other embodiments of the present disclosure, referring to FIG. 12, the ultrasound image acquisition system 8 may further comprise a probe 85, and the processor 84 may be configured to execute the ultrasound image acquisition program stored in the memory 82 to further implement the following steps:

transmitting first ultrasonic waves to the inside of the object to be detected by the probe 85 in the first mode;

acquiring first ultrasonic echoes of the first ultrasonic waves to acquire first ultrasonic echo signals, and acquiring a first basic ultrasound image according to the first ultrasonic echo signals; and analyzing the first basic ultrasound image to acquire the first spatial position information inside the object to be detected.

The probe 85 may be an ultrasound probe.

In other embodiments of the present disclosure, the processor 84 may be configured to perform analysis on the first basic ultrasound image stored in the memory 82 to acquire the first spatial position information of the inner of the object to be detected, and may further implement the following steps:

analyzing the first basic ultrasound image, and acquiring first spatial position information of the sub-object to be detected included in the object to be detected in the internal space of the object to be detected.

In other embodiments of the present disclosure, the processor 84 may be configured to execute the ultrasound image acquisition program stored in the memory 82 to further implement the following steps:

switching the operating mode of the ultrasound image acquisition system from the first mode to a second mode in which a planar image is acquired;

acquiring at least one target acquisition direction according to the first spatial position information inside the object to be detected;

acquiring planar position information inside the object to be detected along the at least one target acquisition direction in the second mode; and generating a second planar ultrasound image of the inside of the object to be detected according to the planar position information and displaying it on the display.

In other embodiments of the present disclosure, the processor 84 may be configured to execute the first spatial position information on the basis of the inner of the object to be detected stored in the memory 82 to acquire at least one target acquisition direction, and may further implement the following steps:

receiving a second acquisition instruction which is used for collecting the planar image of the inside of the object to be detected and carries identification information of the sub-object to be detected; and determining the at least one target acquisition direction according to the identification information and the first spatial position information inside the object to be detected.

In other embodiments of the present disclosure, the processor 84 may be configured to execute the step (stored in the memory 82) of acquiring the planar position information inside the object to be detected along at least one target acquisition direction in the second mode and may further implement the following steps:

transmitting second ultrasonic waves to the inside of the object to be detected along the at least one target acquisition direction by the probe in the second mode;

acquiring second ultrasonic echoes of the second ultrasonic waves to acquire second ultrasonic echo signals; and acquiring the planar position information inside the object to be detected along the at least one target acquisition direction according to the second ultrasonic echo signals.

In other embodiments of the present disclosure, the processor 84 may be configured to execute the ultrasound image acquisition program stored in the memory 82 to further implement the following steps:

displaying the plane position information.

In other embodiments of the present disclosure, the processor 84 may be configured to execute the ultrasound image acquisition program stored in the memory 82 to further implement the following steps:

storing the first spatial position information inside the object to be detected.

In other embodiments of the present disclosure, the processor 84 may be configured to execute the ultrasound image acquisition program stored in the memory 82 to further implement the following steps:

acquiring the first spatial position information inside the object to be detected stored in the ultrasound image acquisition system according to a received third acquisition instruction used for collecting object to be detected;

acquiring second spatial position information inside the object to be detected on the basis of the third acquisition instruction according to the stored first spatial position information inside the object to be detected; and generating a second three-dimensional ultrasound image on the basis of the inside of the object to be detected according to the second spatial position information inside the object to be detected and displaying it on the display.

In other embodiments of the present disclosure, the processor 84 may be configured to execute the step (stored in the memory 82) of acquiring the first spatial position information inside the object to be detected stored in the ultrasound image acquisition system according to a received third acquisition instruction used for collecting object to be detected and may further implement the following steps:

according to a received third acquisition instruction used for collecting object to be detected, acquiring the first spatial position information inside the object to be detected stored in the ultrasound image acquisition system and a second basic ultrasound image of the inside of the object to be detected.

Correspondingly, in other embodiments of the present disclosure, the processor 84 may be configured to execute the step (stored in the memory 82) of acquiring the second spatial position information inside the object to be detected on the basis of the third acquisition instruction according to the stored first spatial position information inside the object to be detected, and may further implement the following steps:

acquiring the second spatial position information inside the object to be detected on the basis of the third acquisition instruction according to the stored first spatial position information inside the object to be detected and the second basic ultrasound image.

In other embodiments of the present disclosure, the processor 84 may be configured to execute the ultrasound image acquisition program stored in the memory 82 to further implement the following steps:

displaying the first spatial position information inside the object to be detected on the display and receiving a modification operation on the basis of the first spatial position information inside the object to be detected; and modifying the first spatial position information inside the object to be detected according to the modification operation, and displaying the modified first spatial position information inside the object to be detected.

In other embodiments of the present disclosure, the processor 84 may be configured to execute the ultrasound image acquisition program stored in the memory 82 to further implement the following steps:

generating the first three-dimensional ultrasound image of the inside of the object to be detected according to the modified first spatial position information inside the object to be detected and displaying it on the display.

In other embodiments of the present disclosure, the processor 84 may be configured to execute the ultrasound image acquisition program stored in the memory 82 to further implement the following steps:

acquiring the at least one target acquisition direction according to the modified first spatial position information inside the object to be detected.

In other embodiments of the present disclosure, the processor 84 may be configured to execute the ultrasound image acquisition program stored in the memory 82 to further implement the following steps:

detecting and analyzing the object to be detected according to the first spatial position information inside the object to be detected.

In other embodiments of the present disclosure, the processor 84 may be configured to execute the ultrasound image acquisition program stored in the memory 82 to further implement the following steps:

detecting and analyzing the object to be detected according to the planar position information inside the object to be detected along the at least one target acquisition direction.

It should be noted that, for the specific implementation of the steps executed by the processor 84 in this embodiment, reference may be made to the specific implementation of the ultrasound image acquisition methods provided in the embodiments shown in FIGS. 2-4, 8, which will not be repeated here.

In the ultrasound image acquisition system provided by the embodiments of the present disclosure, the spatial position information of the inner of the object to be detected can be automatically obtained in a mode configured to collect stereoscopic spatial images, solving a problem that an operator needs to manually analyze obtained image data to acquire the internal spatial position information of the organ when using 4D ultrasound technology, achieving automatic analysis of the image data to acquire the spatial position information, and improving the accuracy of the acquired spatial position information.

Based on the foregoing embodiment, an ultrasound image acquisition system, which may be applied to the ultrasound image acquisition methods corresponding to the embodiments shown in FIGS. 10-11, may be provided in the embodiment of the present disclosure provides. Still referring to FIG. 12, the ultrasound image acquisition system 8 may at least include: a display 81, a memory 82, a communication bus 83, a processor 84 and a probe 85.

The memory 82 may be configured to store an ultrasound image acquisition program.

The communication bus 83 may be configured to realize connection and communication between the processor 84 and the memory 82.

The processor 84 may be configured to execute the ultrasound image acquisition program stored in the memory 82 to implement the following steps:

according to a received first acquisition instruction used for scanning an object to be detected, determining the operating mode of the ultrasound image acquisition system to be a first mode in which a three-dimensional image is acquired;

transmitting first ultrasonic waves to the inside of the object to be detected by the probe 85 in the first mode;

receiving first ultrasonic echoes which is returned from the inside of the object to be detected and based on the first ultrasonic waves by the probe 85, acquiring first ultrasonic echo signals and performing beamforming on the first ultrasonic echo signals to acquire a plurality of first basic ultrasound images;

acquiring a first reference direction and a contour of a reference sub-object to be detected according to the plurality of first basic ultrasound images;

acquiring first spatial position information inside the object to be detected according to the first reference direction and the contour of the reference sub-object to be detected;

generating a three-dimensional ultrasound image and/or a first planar ultrasound image of the inside of the object to be detected according to the first spatial position information inside the object to be detected; and displaying the three-dimensional ultrasound image and/or the first planar ultrasound image, and displaying the first spatial position information in the form of a graphical interface.

In other embodiments of the present disclosure, the processor 84 may be configured to execute the ultrasound image acquisition program stored in the memory 82 to further implement the following steps:

detecting and analyzing the contour of a sub-object to be detected included in the plurality of first basic ultrasound image to acquire a plurality of first basic contours of the reference sub-object to be detected;

analyzing the plurality of first basic ultrasound images and the plurality of first basic contours of the reference sub-object to be detected to acquire a second reference direction; and acquiring the first reference direction and the contour of the reference sub-object to be detected according to the second reference direction and the plurality of first basic contours of the reference sub-object to be detected.

In other embodiments of the present disclosure, the processor 84 may be configured to execute the ultrasound image acquisition program stored in the memory 82 to further implement the following steps:

synthesizing the plurality of first basic contours of the reference sub-object to be detected to acquire a second basic contour of the reference sub-object to be detected;

analyzing the plurality of first basic ultrasound images according to the second basic contour of the reference sub-object to be detected and the second reference direction to acquire a basic position of the sub-object to be detected included in the object to be detected; and calibrating the first basic contours of the reference sub-object to be detected and the second reference direction according to the basic position of the sub-object to be detected to acquire the first reference direction and the contour of the reference sub-object to be detected.

In other embodiments of the present disclosure, the processor 84 may be configured to execute the ultrasound image acquisition program stored in the memory 82 to further implement the following steps:

rotating the plurality of first basic ultrasound images along the first reference direction to acquire a plurality of target basic ultrasound images;

recognizing the plurality of target basic ultrasound images to acquire a specific three-dimensional ultrasound image; and analyzing and fusing the specific three-dimensional ultrasound image according to the contour of the reference sub-object to be detected to acquire first spatial position coordinates of the sub-object to be detected included in the object to be detected in the internal space of the object to be detected, wherein the first spatial position information includes the first spatial position coordinates.

In other embodiments of the present disclosure, the memory 82 may also implement the following steps:

storing the first spatial position information inside the object to be detected.

In other embodiments of the present disclosure, the processor 84 may be configured to execute the ultrasound image acquisition program stored in the memory 82 to further implement the following steps:

according to a received third acquisition instruction used for collecting object to be detected, acquiring the first spatial position information inside the object to be detected stored in the ultrasound image acquisition system and a second basic ultrasound image of the inside of the object to be detected;

determining a transformation matrix between the first basic ultrasound image and the second basic ultrasound image;

according to the transformation matrix and the first spatial position information, acquiring a second spatial position information inside the object to be detected according to the third acquisition instruction; and according to the second spatial position information inside the object to be detected, generating and displaying a second three-dimensional ultrasound image of the inside of the object to be detected.

In other embodiments of the present disclosure, the display 81 may also implement the following steps:

displaying the relationship among spatial positions of each three-dimensional ultrasound image of the first three-dimensional ultrasound image;

and/or displaying the relationship among planar positions of each planar ultrasound image of the first planar ultrasound image.

In other embodiments of the present disclosure, the processor 84 may be configured to execute the ultrasound image acquisition program stored in the memory 82 to further implement the following steps:

according to the first spatial position information inside the object to be detected, on the basis of the first ultrasonic echo signals, generating the first three-dimensional ultrasound image and/or the first planar ultrasound image of the inside of the object to be detected;

or, transmitting second ultrasonic waves to the inside of the object to be detected according to the first spatial position information inside the object to be detected, receiving second ultrasonic echoes which is returned from the inside of the object to be detected and based on the second ultrasonic waves to acquire second ultrasonic echo signals, and generating the first three-dimensional ultrasound image and/or the first planar ultrasound image of the inside of the object to be detected according to the second ultrasonic echo signals, wherein the second ultrasonic waves are different from the first ultrasonic waves.

It should be noted that, for the specific implementation of the steps executed by the processor 84 in this embodiment, reference may be made to the specific implementation of the ultrasound image acquisition methods provided in the embodiments shown in FIGS. 10-11, which will not be repeated here.

It should be noted that when the above ultrasound image acquisition method is implemented in the form of a software functional module and sold or used as an independent product, it can also be stored in a computer readable storage medium. Based on this, the technical solutions of the embodiments of the present disclosure can be embodied in the form of a software product in essence or a part that contributes to the prior art. The computer software product which may be stored in a storage medium may include several instructions so that a computer device (which may be a personal computer, a server, or a network device, etc.) can execute all or part of the methods described in the various embodiments of the present disclosure. The aforementioned storage medium may include: U disk, mobile hard disk, read only memory (ROM), magnetic disk or optical disk and other media that can store program codes. In this way, the embodiments of the present disclosure are not limited to any specific combination of hardware and software.

Correspondingly, a computer-readable storage medium storing computer-executable instructions is provided in an embodiment of the present disclosure, wherein when being executed by a processor, the computer-executable instructions may realize the steps in the ultrasound image acquisition methods mentioned above.

The embodiments about the computer program product, computer equipment, and computer storage medium are described similar to the embodiments of methods mentioned above, accordingly they has similar beneficial effects as the method embodiment. For technical details not disclosed in the embodiments of the computer program product, computer equipment, and computer storage medium of the present disclosure, please refer to the description of the method embodiments of the present disclosure for understanding.

It should be understood that "an embodiment" or "an example" mentioned throughout the specification means that a specific feature, structure, or characteristic related to the embodiment is included in at least one embodiment of the present disclosure. Therefore, terms "in one embodiment" or "in an example" appeared herein do not necessarily refer to an identical embodiment. In addition, these specific features, structures or characteristics can be combined in one or more embodiments in any suitable manner. It should be understood that in the various embodiments of the present disclosure, the sequence numbers of the above-mentioned processes does not mean the order of execution. The execution sequence of each process shall be determined by its function and internal logic, and shall not constitute any limitation to the implementation process of the embodiments of the present disclosure. The serial numbers of the foregoing embodiments of the present disclosure are only for description, and do not represent the superiority of the embodiments.

It should be noted that in the present disclosure, the terms "comprise", "include" or any other variants thereof are intended to cover non-exclusive inclusion, so that a process, method, article or device including a series of elements not only includes those elements, but also includes other elements that are not explicitly listed, or elements inherent to the process, method, article, or device. If there are no more restrictions, the element defined by the sentence "including a . . . " does not exclude the existence of other similar elements in the process, method, article, or device that includes the element.

It should be understood that the systems and methods disclosed in the embodiments provided herein can be implemented in other ways. The systems described in above embodiments are merely illustrative. For example, the units may be divided only in a logical function manner, and there may be other divisions in practice, such as: combining multiple units or components, or integrating them into another system, or omitting some features or not implementing them. In addition, the coupling, or direct coupling, or communication connection among the components shown or discussed may be implemented through some interfaces, systems or units in a direct or indirect manner and may be in electrical, mechanical or other forms.

The units described above as separate components may or may not be physically separate, and the components displayed as units may or may not be physical units. They may be located in one place or distributed on multiple network units; and some or all of the units can be selected according to actual needs.

In addition, the functional units in the embodiments of the present disclosure can be all integrated into one processor, or each unit can be individually used as a unit, or two or more units can be integrated into one unit. The integrated unit can be implemented in the form of hardware, or in the form of hardware plus software functional units.

Those skilled in the art may understand that all or part of the steps of the above methods can be implemented by a relevant program instructing hardware. The foregoing program can be stored in a computer readable storage medium, and when the program is executed, the steps of the foregoing methods can be executed. The foregoing storage medium may include: portable storage devices, read only memory (ROM), magnetic disks, or optical disks, and other media that can store program codes.

Alternatively, when the above-mentioned integrated unit of the present disclosure is implemented in the form of a software functional module and sold or used as an independent product, it may also be stored in a computer readable storage medium. Based on this, the technical solutions of the embodiments of the present disclosure can be embodied in the form of a software product in essence or a part that contributes to the prior art. The computer software product which may be stored in a storage medium may include several instructions so that a computer device (which may be a personal computer, a server, or a network device, etc.) can execute all or part of the methods described in the various embodiments of the present disclosure. The aforementioned storage medium may include: U disk, mobile hard disk, read only memory (ROM), magnetic disk or optical disk and other media that can store program codes. In this way, the embodiments of the present disclosure are not limited to any specific combination of hardware and software.

The above are only the implementation manners of present disclosure, but the protection scope of present disclosure is not limited to this. Any person skilled in the art can easily conceive of changes or substitutions within the technical scope disclosed in the present disclosure, and they should be covered by the protection scope of the present disclosure. Therefore, the protection scope of the present disclosure should be subject to the protection scope of the claims.

INDUSTRIAL APPLICABILITY

The ultrasound image acquisition methods in the embodiments of the present disclosure include: according to a received first acquisition instruction used for scanning an object to be detected, setting the operating mode of the ultrasound image acquisition system to be a first mode in which a three-dimensional image is acquired; and acquiring first spatial position information inside the object to be detected in the first mode. In this respect, the spatial position information of the inner of the object to be detected can be obtained in a mode configured to collect 3D spatial images, ensuring the comprehensiveness and accuracy of the obtained data.

The invention claimed is:
1. An ultrasound image acquisition method, applied to an ultrasound image acquisition system, comprising:
  according to a received first acquisition instruction used for scanning an object to be detected, setting an operating mode of the ultrasound image acquisition system to be a first mode in which a three-dimensional image is acquired;
  acquiring a first spatial position information inside the object to be detected in the first mode;
  generating at least one of a first three-dimensional ultrasound image or a first planar ultrasound image of an inside of the object to be detected based on the first spatial position information inside the object to be detected;
  switching the operating mode of the ultrasound image acquisition system from the first mode to a second mode in which a planar image is acquired;
  receiving a second acquisition instruction which is used for collecting the planar image of the inside of the object to be detected and includes an identification information of a sub-object to be detected, wherein the identification information is used for identifying at least one of views of a heart;
  determining at least one target acquisition direction according to the identification information given by a user and the first spatial position information obtained in the first mode;
  in response to the user selecting one of the views of the heart, acquiring a planar position information inside the object to be detected along the at least one target acquisition direction in the second mode; and generating and displaying a second planar ultrasound image of the inside of the object to be detected according to the planar position information; and in response to the user selecting multiple views of the views of the heart, acquiring corresponding planar position information inside the object to be detected along target acquisition directions in the second mode; and generating and displaying corresponding views of planar ultrasound images according to the planar position information.

2. The method according to claim 1, further comprising: displaying at least one of: the first three-dimensional ultrasound image or the first planar ultrasound image, and displaying the first spatial position information.

3. The method according to claim 1, wherein the acquiring the planar position information inside the object to be detected along the at least one target acquisition direction in the second mode comprises:

transmitting second ultrasonic waves to the inside of the object to be detected along the at least one target acquisition direction in the second mode;

acquiring second ultrasonic echoes of the second ultrasonic waves to obtain second ultrasonic echo signals; and acquiring the planar position information inside the object to be detected along the at least one target acquisition direction according to the second ultrasonic echo signals.

4. The method according to claim 1, wherein after generating and displaying the second planar ultrasound image of the inside of the object to be detected according to the planar position information, the method further comprises:

displaying the planar position information.

5. The method according to claim 1, wherein after acquiring the first spatial position information inside the object to be detected, the method further comprises:

storing the first spatial position information inside the object to be detected.

6. The method according to claim 1, further comprising: displaying the first spatial position information inside the object to be detected and receiving a modification operation on the basis of the first spatial position information inside the object to be detected; and modifying the first spatial position information inside the object to be detected according to the modification operation, and displaying the modified first spatial position information inside the object to be detected.

7. The method according to claim 6, wherein the generating the first three-dimensional ultrasound image of the inside of the object to be detected based on the first spatial position information inside the object to be detected comprises:

generating the first three-dimensional ultrasound image of the inside of the object to be detected according to the modified first spatial position information inside the object to be detected.

8. The method according to claim 6, wherein the determining the at least one target acquisition direction according to the identification information and the first spatial position information inside the object to be detected comprises:

determining the at least one target acquisition direction according to the identification information and the modified first spatial position information inside the object to be detected.

9. The method according to claim 1, further comprising: detecting and analyzing the object to be detected according to the first spatial position information inside the object to be detected.

10. The method according to claim 1, further comprising: detecting and analyzing the object to be detected according to the planar position information inside the object to be detected along the at least one target acquisition direction.

11. The method according to claim 1, wherein the acquiring the first spatial position information inside the object to be detected in the first mode comprises:

transmitting first ultrasonic waves to the inside of the object to be detected in the first mode;

acquiring first ultrasonic echoes of the first ultrasonic waves to acquire first ultrasonic echo signals, and acquiring a plurality of first basic ultrasound images according to the first ultrasonic echo signals;

acquiring a first reference direction and a contour of a reference sub-object to be detected according to the plurality of first basic ultrasound images; and acquiring the first spatial position information inside the object to be detected according to the first reference direction and the contour of the reference sub-object to be detected.

12. The method according to claim 11, wherein acquiring the first spatial position information inside the object to be detected comprises:

analyzing the plurality of first basic ultrasound images to acquire the first spatial position information of the sub-object to be detected included in the object to be detected in an internal space of the object to be detected.

13. The method according to claim 1, wherein the views of the heart comprise an apical four-chamber (A4C) view, an apical two-chamber (A2C) and an apical long axis (ALAX) view.

14. An ultrasound image acquisition system, at least comprising a display, a memory, a communication bus and a processor, wherein:

the memory is configured to store an ultrasound image acquisition program;

the communication bus is configured to realize connection and communication between the processor and the memory; and the processor is configured to execute the ultrasound image acquisition program stored in the memory to perform operations comprising:

according to a received first acquisition instruction used for scanning an object to be detected, setting an operating mode of the ultrasound image acquisition system to be a first mode in which a three-dimensional image is acquired;

acquiring a first spatial position information inside the object to be detected in the first mode;

generating at least one of a first three-dimensional ultrasound image or a first planar ultrasound image of an inside of the object to be detected based on the first spatial position information inside the object to be detected;

switching the operating mode of the ultrasound image acquisition system from the first mode to a second mode in which a planar image is acquired;

receiving a second acquisition instruction which is used for collecting the planar image of the inside of the object to be detected and carries an identification information of a sub-object to be detected, wherein the identification information is used for identifying at least one of views of a heart;

determining at least one target acquisition direction according to the identification information given by a user and the first spatial position information obtained in the first mode;

in response to the user selecting one of the views of the heart, acquiring a planar position information inside the object to be detected along the at least one target acquisition direction in the second mode; and generating and displaying a second planar ultrasound image of the inside of the object to be detected according to the planar position information; and in response to the user selecting multiple views of the views of the heart, acquiring corresponding planar position information inside the object to be detected along target acquisition directions in the second mode; and generating and displaying corresponding views of planar ultrasound images according to the planar position information.

15. The ultrasound image acquisition system according to claim 14, wherein the operations further comprise:

displaying at least one of: the first three-dimensional ultrasound image or the first planar ultrasound image and displaying the first spatial position information on the display.

* * * * *